(12) United States Patent
Bach et al.

(10) Patent No.: US 7,604,933 B2
(45) Date of Patent: Oct. 20, 2009

(54) METHOD FOR SORTING TUMOR CELLS

(75) Inventors: Ferdinand Bach, Wedel (DE); Joseph Fischer, Freehold, NJ (US)

(73) Assignee: Oncoscience AG, Wedel (DE)

( * ) Notice: Subject to any disclaimer, the term of this patent is extended or adjusted under 35 U.S.C. 154(b) by 0 days.

(21) Appl. No.: 10/556,083

(22) PCT Filed: May 7, 2004

(86) PCT No.: PCT/EP2004/004897

§ 371 (c)(1),
(2), (4) Date: Aug. 31, 2006

(87) PCT Pub. No.: WO2004/099393

PCT Pub. Date: Nov. 18, 2004

(65) Prior Publication Data

US 2007/0042338 A1  Feb. 22, 2007

Related U.S. Application Data (60) Provisional application No. 60/469,200, filed on May 9, 2003.

(30) Foreign Application Priority Data

Sep. 30, 2003  (EP) .................................. 03022146

(51) Int. Cl.
*C12Q 1/00* (2006.01)
*C12N 5/02* (2006.01)
*C12N 5/06* (2006.01)

(52) U.S. Cl. ........................... 435/4; 435/325; 435/374; 435/375

(58) Field of Classification Search ........................ None
See application file for complete search history.

(56) References Cited

U.S. PATENT DOCUMENTS 5,897,987 A  4/1999  Oliver et al.
6,197,575 B1  3/2001  Griffith et al.
6,274,305 B1  8/2001  Sonnenschein et al.
6,368,786 B1  4/2002  Saint-Ramon et al.

FOREIGN PATENT DOCUMENTS

EP  0 377 582  7/1990
WO  WO0240717  *  5/2002

OTHER PUBLICATIONS

Helm et al, International Journal of Clinical Pharmacology and Therapeutics, 2005, vol. 43, pp. 586-587.*
Helm et al, International Journal of Clinical Pharmacology and Therapeutics, 2004, No. 42, pp. 659-660.*
NLM Gateway, Concept Details, downloaded from the Web on Nov. 7, 2008.*
Römp Chemie Lexikon (Jürgen Falbe & Manfred Regitz, 9$^{th}$ ed. 1990) p. 2523, Liposomen (with English Translation).
Florell et al., "Preservation of RNA for Functional Genomic Studies: A Multidisciplinary Tumor Bank Protocol", *Modern Pathology*, 14(2):116-128 (2001).
Goodman & Gilman's The Pharmacological Basis of Therapeutics, (Joel Hardman & Lee Limbird, 10$^{th}$ ed. 2001) Chapters 43-53, pp. 1143-1484.
International Preliminary Report on Patentability for International Application No. PCT/EP2004/004897 completed Apr. 7, 2005.
Tornberg et al., "Functional Characterization of Protein Stabilized Emulsions: Standardized Emulsifying Procedure", *Journal of Food Science*, 43(5):1553-1558 (1978).
Wang et al., "Optimal Procedure for Extracting RNA from Human Ocular Tissues and Expression Profiling of the Congenital Glaucoma gene FOXC1 Using Quantitative RT-PCR", *Molecular Vision*, 7:89-94 (2001).

* cited by examiner

*Primary Examiner*—Karen A Canella
(74) *Attorney, Agent, or Firm*—Arnold & Porter LLP

(57) ABSTRACT

The present invention relates to a method for storing cells, wherein the cells are stored in a composition comprising a base nutritive medium and liposomes at temperatures in the range of −196° C. to 37° C., characterized in that the liposomes comprise one or more sterols and that the cells are tumor cells. More specifically, the invention relates to simple and effective methods for storing tumor cells, wherein the RNA and/or DNA in the cells is essentially not degraded, such that the RNA and/or DNA can be analyzed after storage.

30 Claims, 4 Drawing Sheets

METHOD FOR SORTING TUMOR CELLS

This application is a National Stage application of International Application No. PCT/EP2004/004897, filed May 7, 2004, which claims the benefit of European Patent Application Number 030 22 146.9, filed Sep. 30, 2003, and U.S. patent application Ser. No. 60/469,200, filed May 9, 2003. The disclosures of these applications are hereby incorporated by reference in their entirety.

FIELD OF THE INVENTION

The present invention relates to methods for storing tumor cells, such as tissue samples, biopsies or explants. More specifically, the invention is directed to simple and effective methods of storing tumor cells, wherein the RNA and/or DNA in the cells is essentially not degraded, such that the RNA and/or DNA can be analyzed after storage.

BACKGROUND OF THE INVENTION

Tumor biopsies are often used for diagnostic purposes and for obtaining information on potentially effective therapies. For example, patients likely to respond to particular drugs can be identified by analyzing gene expression levels or patterns of tumor cells. The underlying mutations responsible for tumor growth can be characterized. In a number of tests tumor derived RNA is used as a starting material for the analysis, for example using reverse transcriptase polymerase chain reaction (RT-PCR). Unfortunately however, RNA is known to be particularly unstable.

As it is not always possible to do all necessary tests immediately after obtaining the tumor sample, such as a biopsy, a method of storing the sample is needed. In some cases the necessity for certain tests only becomes clear after some time or new tests are available which one would like to use for the analysis of previous tumors. It would be desirable to store tumor biopsies over an extended period of time.

Several approaches have thus been developed to store tumor cell samples. One method allowing RT-PCR amplification of RNA is deep freezing cells or tissue by immersing it in liquid nitrogen, and storing it at −80° C. To prevent degradation of RNA by RNases, the tissue must be homogenized in the frozen state before being mixed with RNA extraction buffer. With its stringent requirement for liquid nitrogen, the method is labour intensive and unsuitable for preserving tissue samples obtained in a clinical setting.

Often, pathological samples are formalin-fixed and paraffin-embedded (FSPE). These samples can be used for histological analysis, but analysis of RNA poses a problem. Special methods have been developed to extract RNA from such tissues, for example the method developed by K. Dannenberg et al. (U.S. Pat. No. 6,248,535 and U.S. Pat. No. 6,428,963). Again, the method of storage of tumor cells and retrieval of RNA or DNA is a very labour intensive.

Storage in water allows immunohistological analysis of proteins, but RNA is quickly degraded.

One of the standard methods for storage of tumor cells, such as tumor biopsies, uses the liquid composition RNAlater, commercially available from Ambion or Qiagen. As described in U.S. Pat. No. 6,528,64.1, this RNA preservation medium precipitates the RNA in the sample along with the sample protein and thus protects it from RNases. The precipitation is caused by high salt concentrations, typically ammonium sulfate.

RNAlater is not only suitable for extracting and afterwards analyzing RNA from tissues (W-H. Wang et al. (2001), Molecular Vision, vol. 7:89-94), but it is also suitable for storing tissue samples that have to be analyzed histologically or immunohistochemically (S. R. Florell et al. (2001), Mod. Pathol., vol. 14(2):116-128). However, these approaches directly kill the cells in the sample to be stored.

Preserving the viability of the cells would be useful, for example for overcoming limitations of the size of the tissue sample taken. Taking cells into culture would allow to proliferate the same. It would then also be possible to perform assays for biological functions of the cells at a later timepoint, either directly from the culture or after freezing and thawing the cells for further cultivation.

Preservation of viability is of supreme importance for the storage of organs for transplantation. It has been recognized that some of the solutions developed for the perfusion and storage of organs could also be suitable for preserving tissues or culturing cells. For example, U.S. Pat. No. 5,599,659 discloses that a chemically defined cell culture medium, comprising, e.g. retinal-derived fibroblast growth factor, cyclodextrin and chondroitin sulfate, can be used for the preservation of organs or tissues or the culture of vascular endothelial cells.

WO93/09220 refers to a defined basic culture medium with optional addition of growth promoting agents like hem, hemin, IL-3, SCF, EPO, IGF or retinoids that can be used for the mainentance and growth of hematopoetic progenitor cells or leukemia cells.

U.S. Pat. Nos. 6,004,579 and 6,495,532 propose to use liquid compositions comprising liposomes with lysophosphatidic acids for the inhibition of apoptosis. However, these compositions are not ideal for storing tumor cells and have further draw-backs, e.g. the uptake of phospholipids into tissues.

Further, organs on the one hand and healthy or pathological tissue samples and cells on the other differ in their requirements for oxygen and the partial oxygen pressure needed to maintain viability of organs could well damage tissue samples or cells. The problem underlying the present invention thus resides in providing easy and efficient methods for storing tumor cells, which methods enable the analysis of the tumor cells after storage.

The Present Invention

The present invention thus provides a method for storing cells, wherein the cells are stored in a composition comprising a base nutritive medium and liposomes at temperatures in a range of minus 196° C. to 37° C., characterized in that the liposomes comprise one or more sterols and that the cells are tumor cells.

The present inventors have surprisingly found that tumor cells can be stored for extended time periods in a base nutritive medium comprising liposomes comprising one or more sterols without essentially damaging the cells or degrading the RNA and/or DNA therein. The method of the present invention has the specific advantage that tumor cells, such as tumor biopsies can be stored in a single composition at room temperature for several days and even weeks. Tumor biopsies obtained from a patient may thus be stored and analyzed for extended time periods. Tumor biopsies may even be stored in the same composition in the frozen state. This will allow the preparation of tumor biopsy libraries, which can be used for drug target identification and various pharmaceutical research purposes. The preparation of a tumor library will for example allow to correlate the response of a patient treated with a certain drug treatment with a detailed molecular analysis of the tumor sample. This will significantly simplify the optimal treatment strategy for other patients with the same tumor type.

The cells can be stored in the composition in accordance with the methods of the present invention for any period of time, but are preferably stored for a period from at least one or several days up to several years.

According to a specifically preferred embodiment of the present invention the cells can be stored in the present method in such a manner that the RNA and/or DNA in the cells is essentially not degraded during storage. This will allow full analysis of the expression pattern of the tumor cells and classification of the tumor type. In accordance with the present application, the term "the RNA and/or DNA in the cells is essentially not degraded during storage" means that a comparison of the respective molecule type in cells after storage with the cells before storage shows that more than 60% of the RNA and/or DNA can still be analyzed. It is for example possible to analyze the tumor sample quality before storage by analysis of the concentration of a certain RNA, such as RNA encoding a known housekeeping gene expressed in the tissue of interest, via RT-PCR. After storage the test is repeated. The RNA is essentially not degraded during storage in accordance with the use of this term in the present application, when the analysis reveals that the amplification product after storage amounts to at least 60% preferably at least 80% of the amplification product before storage.

Alternatively or additionally the protein expression profile of the cells may be analyzed using any of the large number of methods for analyzing proteins known in the art. Again it is preferred that the proteins are not substantially degraded during storage. The cells may further be analyzed via histological staining or in situ hybridization after storage.

According to an especially preferred embodiment of the present invention the tumor cells can be stored in such a manner that they are still capable of proliferation after storage. For this purpose, the tumor cells can be isolated from the tissue if necessary and can be propagated according to well known techniques in a cell culture medium. The composition used for storing of tumor cells can advantageously also be used for propagation of tumor cells.

According to one aspect of the present invention, the method for storing cells comprises steps, wherein the cells are first stored in the composition at room temperature and subsequently stored in said composition at a temperature in a range of −196 to 0° C. According to a further preferred embodiment the cells are stored in the composition at room temperature for 1 to 14 days and subsequently stored in said composition at a temperature in a range of −196 and 0° C. for at least one month, preferably several years, wherein the RNA and/or DNA in the cells are not essentially degraded during storage. During storage at room temperature the composition may be exchanged when the nutrients are exhausted, such as every 3 days, which will enhance the viability of the cells.

In a further aspect, this invention provides a method for freezing cells of any cell type and storing them in frozen state, wherein the cells are frozen in a composition comprising a base nutritive medium and liposomes, characterized in that the liposomes comprise one or more sterols. Freezing cells immediately in this composition is possible without substantially affecting the viability of the cells, probably because the composition inhibits or reduces cristallisation in the cells. For this reason no additives like DMSO or HES have to be added to the composition to preserve the viability of the cells during freezing or thawing, which makes the method especially suitable when toxicity of DMSO would be problematic, e.g. with sensitive cells.

Therefore, the composition preferably does not contain a cryoprotective agent, such as HES (Hydroxyethylstarch), Glycerol, Arabinogalactan, DMSO (Dimethylsulfoxide) or ethylene glycol. Preferably, the composition is free from sera or undefined proteins.

In a preferred embodiment, before freezing, the cells are stored at room temperature in the composition for up to one week or up to 72 hours. Alternatively, the cells can also be stored at 4° C. before freezing.

The cells can be frozen or thawed by the methods commonly used by the person skilled in the art. Although a special freezing of thawing protocol is thus not necessary for carrying out the method of the invention, the cells are preferably frozen over 60 minutes (min) to −120° C. and then transferred to liquid nitrogen. In a preferred embodiment, the cells are frozen with the following freezing protocol, using a computer-controlled cold block: First, the tissue is held for 15 min at 4° C., thereafter, frozen at a rate of −99° C./min to −5° C., with −0.5° C./min to −7° C., with −30° C./min to −60° C., with 8,4° C./min to −18° C., held at −18° C. for 3 min, frozen with −2° C./min to −40° C., with −4° C./min to −80° C., with −10° C. to −120° C. and thereafter in liquid nitrogen to temperatures between −170° C. and −196° C.

Preferably, the temperature for long-term storage of the cells in the composition is −170° C. to −196° C. Cells are preferably stored in liquid nitrogen, e.g., in "Biosafe" cryo-tanks.

In accordance with the present invention the term "base nutritive medium" refers to a composition comprising amino acids, salts, vitamins, nucleotides, carbohydrates and/or antioxidants. The base nutritive medium will typically be a liquid composition.

The medium used in the methods of the present invention may additionally contain any number of compounds which are also suitable for storing tumor cells. Specifically it is preferred that the medium comprises one or more antimicrobial agents and/or growth factors. According to a further preferred embodiment the growth factors comprise epithelial growth factor, hepatocyte growth factor, platelet derived epithelial growth factor and/or vascular endothelial growth factor. The composition preferably does not contain any lysophosphotidic acids.

Liposomes in a water-based solution, as mentioned above, are present as lipid vesicles with a concentric lipid bilayer surrounding a hydrophilic core (Ed.: Falbe, Regitz, Römpp-Chemie-Lexikon, 1990, Georg Thieme Verlag, Stuttgart).

The liposomes in the composition used in the methods of the present invention comprise one or more sterols. Preferably, the sterols comprise cholesterol.

According to a specifically preferred embodiment the methods of the present invention are carried out using the Liforlab composition, containing the substances as described in tables 1-4 below.

The tumor cells may be any tumor cell such as tumor cells derived from a tumor cell line or a tumor tissue, such as a tumor biopsy or a tumor explant. According to a preferred embodiment the tumor cells are a tumor biopsy.

The tumor cells are preferably derived from a human or a mammal and the tumor is preferably a solid tumor, such as a melanoma or a renal cell, stomach, breast, oesophagus or colon carcinoma.

According to a further preferred embodiment, the method of the present invention comprises steps, wherein
(a) a tumor biopsy is derived from a human;
(b) the biopsy is stored in a composition comprising liposomes comprising cholesterol at room temperature for 1 to 14 days; and (c) the biopsy is subsequently stored in the said composition at a temperature in the range of −196 and 0° C. for at least 1 month, preferably several years;
and wherein the RNA and/or DNA in the cells is essentially not degraded during storage. Preferably, the cells are still capable of proliferation after storage.

This way of proceeding allows a specifically advantageous collection of tumor biopsies directly after explantation, forwarding of the tumor biopsies via courier or regular mail (at room temperature) to a diagnostic laboratory and/or long term storage of the tumor biopsy in the frozen state as well as analysis of the tumor type for correlating the tumor type to the patient response to a certain drug treatment.

A further advantage of such storage is that it would make genomic and proteomic analysis of tumor samples in comparison to the complementary non-tumor tissue of the same individuum possible. Non-tumor tissue can either be from a fresh biopsie or it can be stored in parallel with the tumor sample.

According to a further aspect the present invention is directed to the use of a composition for storing cells, wherein the composition comprises a base nutritive medium as defined above and liposomes characterized in that the liposomes comprise one or more sterols and that the cells are tumor cells.

In a further aspect, the present invention is directed to a composition comprising tumor cells, a base nutritive medium and liposomes which liposomes comprise one or more sterols. The tumor cells in this composition are preferably tumor biopsies.

According to a preferred embodiment, the composition comprises tumor biopsies, liposomes which comprise cholesterol and one or more growth factors, preferably epithelial growth factor, hepatocyte growth factor, platelet derived epithelial growth factor and/or vascular endothelial growth factor, and a base nutritive medium which comprises amino acids, salts, vitamins, nucleotides, carbohydrates, anti-oxidants.

In a related aspect, the invention is directed to a library of tumor biopsies comprising a number of different biopsies in a compositios as defined above stored in separate containers.

The present invention is further directed to the use of a respective library of tumor biopsies for diagnostic screening methods, drug efficacy validation and/or in methods for identifying anti-tumor drug targets.

For example, cells from the library of tumor biopsies could be thawed, taken into culture and implanted in nude mice. Thus, they would be available for drug screening, on one hand, to test if certain drugs are effective with this particular tumor, and on the other hand, to screen a library of potential active substances against certain tumors. A drug would be considered to be effective against the tumor, e.g. if the growth of the tumor is slowed, the number of metastases is lower or the tumor regresses partly or totally in a significant percentage of mice as compared with control animals not treated with the drug.

According to this embodiment, the invention is directed to a process for the preparation of a pharmaceutical composition for the treatment of tumor, comprising the use of tumors biopsies from a library of tumor biopsies according to claim 28 for screening of active anti-tumor substances and formulating the active substance thus identified with suitable pharmaceutical additives or carriers to obtain a pharmaceutical composition.

In a general aspect the present invention provides the use of a two-phase liquid composition for storing and stabilizing tumor tissue, wherein the first phase of the liquid composition comprises a base nutritive medium and the second phase comprises liposomes. The base nutritive medium comprises physiologically compatible concentrations of water-soluble or dispersible nutrients and physiological salts, for example amino acids, salts, vitamins, nucleotides, carbohydrates and anti-oxidants. The liposomes of the second phase are nanoparticles which comprise sterols, preferably cholesterol, and, optionally, fatty acids and cellular growth factors. The supposed structure of the liposomes comprises an outer lipophilic coating and an inner hydrophilic core.

The two phase composition used in the invention has an osmolality of at least about 300 mOsM/kg. Preferably, the two phase composition has an osmolality ranging from about 385 to 425 mOsM/kg. The pH of the two phase composition preferably is from about 7.2 to about 7.4. The nanoparticles preferably have a mean diameter ranging from about 100 nm to about 300 nm, more preferably from about 100 nm to about 200 nm.

The composition used in the invention can contain trace elements, simple carbohydrates, buffers, plasma volume expanders, energy substrates, xanthine oxidase inhibitors and the like, dissolved or dispersed in aqueous medium.

In a preferred embodiment, the base nutritive medium includes, in physiologically suitable concentrations, salts, water soluble vitamins, amino acids and nucleotides. These may include, simply by way of example, and without limitation, adenosine and its phosphates, uridine and its phosphate, other nucleotides and deoxynucleotides; B vitamins, e.g., B1, B2, B6, B12, biotin, inositol, choline, folate, and the like; vitamin coenzymes and cofactors, e.g. nicotinamide and flavin adenine dinucleotides, and their respective phosphates, coenzyme A and the like; various physiological salts and trace minerals, e.g. salts of sodium, potassium, magnesium, calcium, copper, zinc and iron; the essential amino acids, although all twenty naturally-occurring amino acids, and/or derivatives thereof, are optionally included. The base medium also includes e.g. pH buffers, such as phosphate buffers and N-2-hydroxyethyl-piperazine-N'-2-ethanesulfonic acid ("HEPES") buffer; simple sugars, e.g., glucose; osmotic enhancers, such as any suitable dextran, mannose and the like; as well as optional miscellaneous components, such as allopurinol, chondrotin, cocarboxylase, physiological organic acids, e.g. pyruvate, and optionally, a nutritive extract from natural sources, e.g., a yeast vitamin extract.

Thus, the base nutritive medium contains numerous nutrient and mineral factors at concentrations analogous to those found in blood, serum, plasma and/or normal body tissues, although certain of these are not natural blood components.

Optionally, the composition used in the invention can further include antimicrobial agents, such as antibiotics, antibacterials, specific antibodies and/or other known agents for controlling microbial contamination in organs, tissues and/or cells. Most known antimicrobials are referenced, in detail, by Goodman & Gilman's, The pharmacological basis of therapeutics, 10th ed., McGraw Hill, especially chapters 43 to 51.

The composition may further contain anti-coagulant, thrombolitic and/or antiplatelet drugs, e.g. heparin and related glycosaminoglycans, dicumarol, phenprocoumon, acenocoumarol and ethyl biscoumacetate, indandione, and derivatives thereof, and aspirin and dipyridamole, and the like. Non-steroidal antiinflammatory agents are also optionally included.

In one alternative embodiment, vitamin C (ascorbate) is optionally included in physiological or higher than physiological concentrations.

Many commercially available cell or tissue culture media products that are free of undefined proteins or animal sera can be adapted to serve as the base nutritive medium or starting point for preparation of the inventive composition, provided that such media are compatible with the specific requirements of the use of the composition.

The second phase of the composition is a liquid-aqueous emulsion comprising liposomes or nano-scale particles that are supposed to have a lipophilic outer layer and a hydrophilic core. Generally, the second phase includes lipophilic components able to form and stabilize the outer, lipophilic layer, including, for example, cholesterol, posphatidylcholine, vitamin E, cod liver oil, etc. Additional components include lipid-based energy sources, including physiologically compatible amounts of free fatty acids.

Preferably, the liposomes of the two phase composition comprise free fatty acids selected from the group consisting of oleic acid, linoleic acid, palmitic or stearic acid, myristic acid, lauric acid, eicosapentaenoic acid, docosahexaenoic acid, and combinations thereof.

Preferably, the two phase composition does not comprise a pharmaceutically significant quantity of phosphatidic acid or sugar, or lysophosphotidic acid or sugar.

In another preferred embodiment, the second phase includes hydrophilic supportive endocrine factors such as hydrocortisone, thyroxine, or its derivatives, and the like. Further supportive components include cellular growth factors, e.g. epithelial and endothelial growth factors, including physiolgically compatible amounts of vascular endothelial growth factor, platelet derived endothelial growth factor, epithelial growth factor, hepatocyte growth factor, platelet derived-endothelial growth factor, and the like. Optionally, other factors contemplated to be included in the second phase include inter-cellular messengers such as prostaglandins, e.g. prostaglandin E1. Preferably, physiologically compatible surfactants and detergents are also included, e.g. one or more water-soluble surfactant, preferably an amphiphilic block copolymer with a molecular weight of several thousand Daltons, such as a polypropyleneoxide-polyethyleneoxide block copolymer surfactant (e.g. Pluronic F-68; from BASF) and/or nonionic surfactants. Suitable nonionic surfactants include, e.g. polyoxyethylene derivatives of sorbitol esters, e.g. polyoxyethylene sorbitan monooleate surfactants that are commercially available as TWEEN® (Atlas Chemical Co.). TWEEN 80® is particularly preferred.

Oxygen that is supposed to be associated with the liposomes plays an important role in keeping up the metabolism of the cells. Of note, even though no additional step of enrichment with oxygen is necessary for the methods of the present invention, such enrichment could be beneficial for enhancing the viability of tumor cells, especially those with a high rate of proliferation or a high metabolic turnover. The content of oxygen comprised in the composition can thus be optimised for different tumors.

Oxygen can be enriched by bubbling air or oxygen through the solution. The amount of oxygen that is taken up by the composition also depends on the amount of sterols or cholesterol comprised in the composition. The amount of sterols in the liposomes, the amount of liposomes or both can be varied to reach optimal results with different tumors. In a preferred embodiment of the invention, the composition is enriched with oxygen. The composition comprises, e.g., at least 0.00475 g/L cholesterol, in particular at least 0.00525 g/L cholesterol, and is enriched with oxygen. Preferably, oxygen is bubbled through the composition until it is saturated with oxygen. Optimal, minimal and maximal amounts of cholesterol and of oxygen can easily be tested for different tumor tissues.

Preparation of the Composition

U.S. Provisional Patent Application No. 60/469,200 discloses that the compositions used in the methods of the present invention can be used to preserve the viability of organs and tissues.

The compositions for use in the invention are generally produced by a two-step process. The first step is to prepare a pre-mix for the first phase, which is the above-described base nutritive medium, designated as Premix-I, herein, and to prepare a premix for the second phase, designated as Premix-II, herein, in which the desired components are premixed, dissolved and/or suspended in water. The Premix-II composition is then processed through a microfluidizer or similar such apparatus, under conditions effective to provide a finely divided emulsion, e.g. a nanoparticle-scale emulsion. The resulting emulsion composition is then mixed with Premix-I, which provides various trace nutrients, and other components, to complete the production of the inventive composition.

Preparation of the Premix Compositions

Tables 1-4, below, summarize the preferred components and weight ranges for Premix I and Premix II, listed together. The components listed by Table 1-4 are the quantities found in one liter of the final composition, after all processing is completed. These components are sorted into these tables for convenience of description, in order to group the components by the way in which the composition is prepared in the examples discussed herein below. Unless otherwise indicated, all quantities shown in Tables 1-4 are in grams per liter of the final composition, i.e. the composition that includes both the aqueous phase and the emulsion phase.

Component quantities set forth by Tables 1-4 are based upon a total batch volume of 1 liter. As exemplified herein, the 1 liter batch volume is the end volume after both Premix-I and Premix-II are combined, wherein Premix-II has been processed into a microscale or nanoscale emulsion. The artisan will appreciate that the processes described are readily scaled up or down for smaller or larger batch sizes, depending on need.

All chemicals used in the preparation of the composition are of substantial purity and available from numerous commercial suppliers of biochemicals. Preferably, these are of USP grade or equivalent. Water should be WFI (Water for injection) grade, preferably USP grade. The artisan will appreciate that the employed chemicals are optionally substituted by substantially equivalent chemicals demonstrating the same purity and activity.

TABLE 1

| Substance | g/L - CONCENTRATION - |
|---|---|
| Adenine HCl | 0.00019-0.00021 |
| B-12 | 0.00065-0.0007 |
| Biotin | 0.00000038-0.00000042 |
| Cupric Sulfate | 0.00000124-0.00000137 |
| Ferric Nitrate | 0.000048-0.000053 |
| Ferric Sulfate | 0.00048-0.00053 |
| Putrescine HCl | 0.000077-0.000085 |
| Pyridoxine HCl | 0.000029-0.000033 |
| Riboflavin | 0.00021-0.000231 |
| Thymidine | 0.00035-0.00039 |
| Zinc Sulfate | 0.00041-0.000454 |

TABLE 2A

| Substance | g/L - CONCENTRATION - |
|---|---|
| Adenosine | 0.950-1.050 |
| Adenosine 5' Monophosphate | 0.0019-0.0021 |
| Adenosine Triphosphate | 0.0019-0.0021 |
| Allopurinol | 0.133-0.147 |
| B'Nicotinamide Adenine Dinucleotide Phosphate | 0.038-0.042 |
| B'Nicotinamide Adenine Dinucleotide | 0.0019-0.0021 |
| Calcium Chloride | 0.152-0.168 |
| Choline Chloride | 0.0085-0.0094 |
| Chondrotin Sulfate | 0.0038-0.0042 |
| Cocarboxylase | 0.038-0.042 |
| Coenzyme A | 0.0095-0.00105 |
| Cyclodextrin | 0.475-0.525 |
| Deoxyadenosine | 0.038-0.042 |
| Deoxycytidine | 0.038-0.042 |
| Deoxyguanosine | 0.038-0.042 |
| Dextran 70 | 33.25-36.75 |
| Flavin Adenine Dinucleotide | 0.038-0.042 |
| Folic Acid | 0.0026-0.0028 |
| Glucose | 3.800-4.200 |
| Glutathione | 0.950-1.050 |
| Glycine | 0.0179-0.0197 |

TABLE 2B

| Substance | g/L - CONCENTRATION - |
|---|---|
| Heparin | 0.171-0.189 |
| HEPES | 3.396-3.753 |
| Hypoxanthine | 0.002-0.0022 |
| Inositol | 0.0124-0.137 |
| Insulin | 0.0095-0.0105 |
| L-Alanine | 0.00428-0.00473 |
| L-Arginine | 0.141-0.155 |
| L-Asparagine | 0.0076-0.0084 |
| L-Aspartic Acid | 0.064-0.070 |
| L-Cysteine | 0.0297-0.0329 |
| L-Cystine | 0.0167-0.0185 |
| L-Glutamic Acid | 0.007-0.0078 |
| L-Glutamine | 4.750-5.250 |
| L-Histidine | 0.030-0.033 |
| L-Isoleucine | 0.052-0.0572 |
| L-Leucine | 0.057-0.063 |
| L-Lysine | 0.0095-0.0105 |
| L-Methionine | 0.019-0.021 |
| L-Phenylalanine | 0.0337-0.0373 |
| L-Proline | 0.0164-0.0182 |
| L-Serine | 0.025-0.0276 |
| L-Threonine | 0.051-0.056 |

TABLE 2C

| Substance | g/L - CONCENTRATION - |
|---|---|
| L-Tryptophan | 0.009-0.0095 |
| L-Tyrosine | 0.053-0.059 |
| L-Valine | 0.050-0.055 |
| Magnesium Chloride | 0.058-0.0643 |
| Magnesium Sulfate | 0.0475-0.0525 |
| Mannose | 3.135-3.465 |
| Niacinamide | 0.0019-0.0021 |
| Panthothenic Acid | 0.0021-0.0024 |
| Potassium Chloride | 0.296-0.328 |
| Pyridoxal HCl | 0.0019-0.0021 |
| Pyruvic Acid | 0.209-0.231 |
| Sodium Bicarbonate | 1.140-1.260 |
| Sodium Chloride | 6.650-7.350 |
| Sodium Phosphate Dibasic | 0.0676-0.0748 |
| Sodium Phosphate Monobasic | 0.0516-0.0570 |

TABLE 2C-continued

| Substance | g/L - CONCENTRATION - |
|---|---|
| Thiamne | 0.0021-0.0023 |
| Transferrin | 0.00475-0.00525 |
| Uridine | 0.038-0.042 |
| Uridine Triphosphate | 0.038-0.042 |
| Yeastolate Ultra-Filtered (Sigma Chemical Company, Cat. No. Y2000) | 38-42 mL |

TABLE 3

| Substance | g/L - CONCENTRATION - |
|---|---|
| L-Cystine | 0.0167-0.0185 |
| L-Tyrosine | 0.053-0.059 |

TABLE 4

| Substance | g/L - CONCENTRATION - |
|---|---|
| Cholesterol | 0.00475-0.00525 |
| Cod Liver Oil | 0.00095-0.00105 |
| Epithelial Growth Factor | 0.00000285-0.00000315 |
| Hepatocyte Growth Factor | 0.0000048-0.0000053 |
| Hydrocortisone | 0.00095-0.00105 |
| Linoleic Acid | 0.00095-0.00105 |
| Linolenic Acid | 0.00095-0.00105 |
| Oleic Acid | 0.00095-0.00105 |
| Phosphatidylcholine | 0.6% |
| Platelet Derived Endothelial Growth Factor | 0.00000095-0.00000105 |
| Pluronic F-68 | 0.950-1.050 |
| Prostaglandin E1 | 0.000042-0.0000263 |
| Triiodo-L-Thyroxine | 0.0000475-0.0000053 |
| TWEEN 80 ® | 0.002375-0.002625 |
| Vascular Endothelial Growth Factor | 0.0000046-0.00000525 |
| Vitamin E | 0.0019-0.0021 |

Process for Making Premix-I

Premix-I is prepared by dissolving or dispersing components in an order that is effective to achieve a uniform and clear aqueous composition, while avoiding undesirable reactions or the formation of insoluble complexes. For this reason, the components in Premix-I are preferably not mixed together until all are fully dissolved or dispersed in water. Preferably, as exemplified herein, the components listed by Tables 1, 2A-2C and Table 3 are processed into three different starting solutions, respectively, although the artisan will appreciate that this base composition is optionally prepared by variations on the exemplified scheme.

The starting solutions are then combined to prepare Premix-I, which constitutes phase 1, i.e. the non-emulsion base nutritive medium.

Process for Making Premix-II

Premix-II includes the emulsion-forming components of the composition. Broadly, these include the hydrophilic layer of the resulting emulsion particle, e.g., components that it is desired to deliver intracellularly. Premix-II also includes the components that form the hydrophobic layer of the resulting emulsion particle, e.g. a lipophilic outer layer that is supposed to allow fusion with living cell membranes for delivery of the hydrophilic core contents, including supportive endocrine factors, suitable agents to aid emulsification, e.g. wetting agent(s) and/or a block copolymer detergent, as well as hydrophobic phase components, such as cholesterol and/or phosphorous derived lipids. Preferably, these are as listed by Table 4, supra and are combined as described by the Examples below.

Microfluidation

The technique of high pressure homogenization, at pressures at or above 5000 psi (344750 hPa) is art-known as "microfluidation". This process was used to create liposomes or nanoparticles with a uniform size distribution of a mean diameter of less than 200 nm. In addition to microfluidation, other standard emulsification methods are optionally employed, e.g. sonication, valve homogenization [Thornberg E. and Lundh, G. (1978) J. Food. Sci. 43:1553] and blade stirring, etc. Desirably, a water soluble surfactant, preferably an amphiphilic block copolymer with a molecular weight of several thousand Daltons, such as a polypropyleneoxide-polyethyleneoxide block copolymer surfactant (e.g. Pluronic F68) and/or TWEEN 80, is added to the aqueous solution in order to stabilize the coated particles against aggregation as they form. The surfactant also serves to enhance the effect of (ultra)sonication, if that method is employed.

A preferred apparatus for microfluidation as exemplified is the Microfluidizer No. HC5000V (Microfluidics Corp., Newton, Mass.) using compressed air supplied by an encapsulated air compressor, e.g. No. ES-6 from Sullair-Solutions (Michigan City, Ind.). The above-described apparatus employs high pressure and high shear homogenization to treat and emulsify the Premix-II composition.

In brief, the Premix-II composition, was processed by high pressure homogenization using the microfluidizer. The Premix-II was added to the microfluidizer reservoir in a continuous fashion, and forced through the specially designed cavitation or interaction chamber, where high shear stress and cavitation forces formed a highly divided emulsion. Through multiple cycles the mean droplet or liposome size, distribution, and combination of ingredients yielded the desired end product, e.g., the preferred nanoparticles.

Further details of the operation of the microfluidizer Model No. HC5000V are provided by the manufacturer's operating manual, available from Microfluidics Corporation, as Cat. No. 85.0112.

EXAMPLES

The following examples illustrate the invention.

Example 1

Preparation of the Liquid Composition Liforlab

Preparation of Premix-I

1. Preparation of Solution 1
   Using an appropriate balance, a 10,000× concentrate of each component listed by Table 1, supra, was prepared. As a convenience, stock solutions for several of these components were prepared in advance, as follows, and an appropriate quantity of stock solution was mixed into Solution 1.
   Cupric Sulfate Stock Solution at 100.000× concentration
   0.130 g of cupric sulfate was weighed and mixed into 1000 ml of WFI gradewater. When necessary, 5N HCl was added dropwise, with mixing, until dissolution was complete. This was mixed until dissolved, and stored at −20° C.
   Ferric Sulfate, Ferric Nitrate and Zinc Sulfate Stock Solution at 10,000× Concentration
   Use 0.1 mL per liter of batch (final volume of end product).
   The stock solution was prepared by weighing out 5.0 g ferric sulfate, 0.5 g ferric nitrate, and 4.3 g zinc sulfate into 1000 mL of WFI grade water. When necessary, the pH was reduced to aid dissolution by adding 5N HCl dropwise until dissolution was complete. This solution was stored at −20° C.
   Biotin Stock Solution at 1000,000× Concentration
   Use 0.01 mL per liter in final solution.
   The biotin stock solution was prepared by weighing out 0.040 g of biotin into 5 mL of WFI grade water. 5N HCl was added dropwise, as needed, during mixing, until dissolution was complete. QS to 1000 mL, and stored at −20° C.
   Vitamin B12 and Thymidine Stock Solution at 1000×
   Use 1 mL per liter in final solution.
   This stock solution was prepared by weighing out 0.670 g vit. B-12 and 0.370 g of thymidine into 1000 mL of WFI grade water, and mixing until dissolution was complete, and stored at −20° C.
   Once all stock concentrates were made, they were added to solution 2 at a volume consistent with their concentration, e.g. 1000×=1 mL per liter etc. The additional components were then added to 1000 mL of WFI grade water and mixed on a magnetic stir plate until dissolution was completed. The resulting solution was added to Solution 2, described below, at a ratio of 0.1 mL per liter of final batch volume (end product).
2. Preparation of Solution 2
   Using the appropriate balance, each component listed by Tables 2A, 2B and 2C. was weighed and added to approximately 50% of the final volume of WFI grade water in final batch volume, i.e. for a 1 liter final batch, solution 2 was prepared to approximately 500 mL of WFI grade water. This was mixed until dissolution was complete.
3. Preparation of Solution 3
   Using the appropriate balance, each component listed by Table 3 was weighed and added to an appropriate sized mixing vessel containing 5% of total batch volume of WFI grade water. While mixing, 5N NaOH was added in a dropwise fashion, until the mixture became clear indicating complete dissolution.

Premix-I was then prepared by taking Solution 1, and combining it with Solution 2, with mixing, in a ratio of 0.1 mL per liter of final batch volume (end product) to form a combined (1+2) solution. Then the entire batch of Solution 3 was mixed with the (1+2) solution to produce Premix-I, that may be used immediately or stored.

Preparation of Premix-II

Component quantities for Premix-II were as set forth by Table 4, supra. For convenience, a number of components of Premix-2 were first prepared as stock solutions, and then employed in appropriate volumes for preparation of Premix-II. The stock solutions were as follows.

Endocrine Factors Stock Solution at 10,000×

Use 0.1 mL per liter in final solution.

This stock solution was prepared by weighing out 0.052 g HGF, 0.050 g triiodo-L-thyroxine, 0.050 g VEGF, and 0.030 g EGF into 1000 mL of WFI grade water, with mixing until dissolution was complete. Batch size was calculated at ×0.1 mL and add to solution in step 4/treatment4. Stored at −20° C.

Hydrocortisone Stock Soluton at 1000×

Use 1 mL per liter in final solution.

This stock solution was prepared by weighing out 0.95 g of hydrocortisone into 10 mL of 95% EtOH and mixing until dissolution was complete. Batch size was calculated at ×1 mL and the stock solution was added to the soluton in step 2, below. Stored at 2-8° C.

Prostaglandin E1 Stock Solution ("PGE1") at 1000×

Use 1 mL per liter in final solution.

Prepared by weighing out 0.034 g PGE1 into 1000 ml of WFI grade water and mixed until dissolution completed. Calculated batch size was ×1 mL and the stock solution was added to solution in step 4, below. Stored at −20° C.

PDGF Stock Solution at 100,000×

Use 0.01 mL per liter in final solution.

This stock solution was prepared by weighing out 0.095 g PDGF into 1000 mL WFI grade water and mixing until dissolution was complete. Batch size was calculated at ×0.01 ml and added to solution in step 4, below. Stored at −20° C.

Premix-II Was Then Prepared by the Following Steps with Components As Set Forth by Table 4, Supra 1. The Pluronic F-68 solution was prepared by weighing out 1 g into less than 50% of total batch volume (based on a 1 liter batch of final product, this was less than 500 mL (of WFI grade water. This was mixed for approximately 1 hour under low heat (less than 100° C.). Mixing was continued until dissolution was complete. The resulting aqueous composition was cooled to approximately 35-40° C. before use.
2. 10 mL of 950 EtOH was measured into a glass mixing vessel and placed on a magnetic stir plate. Phosphatidylcholine was weighed, according to Table 3, and added to this solution, followed by mixing for 1 hour.
3. Cholesterol, linoleic acid, linolenic acid, Vitamin E, TWEEN 80, cod liver oil, hydrocortisone, and oleic acid were weighed, according to Table 4. Preferably, these can be prepared first as a 10,000× concentrate or stock solution to achieve the desired working concentration. These were added to the solution of step 2 and mixed for 1 hour.
4. The solutions of step 2 and 3 were added to the solutions of step 1 and mixed for 1 hour. The resulting composition appeared opaque and cloudy.
5. Hepatocyte growth factor ("HGF"), triiodo-L-Thyroxine, prostaglandin E1, vascular endothelial growth factor ("VEGF"), epithelial growth factor ("EGF"), platelet derived endothelial growth factor ("PDGF") were weighed as indicated. Preferably, these are prepared as a working stock solution of these chemicals.
6. The ingredients of step 5 were added to the solution of step 4 and mixed for 1 hour to produce a Premix-II liquid composition.

Liforlab: Cholesterol-Based Nanoparticles by Microfluidation

Liforlab solution was prepared from the Premix-I and Premix-II compositions, supra, as follows:

1. The air compressor of the microfluidizer was turned on and the line pressure adjusted to 120 PSI at 100 CFM (8274 hPa at 2.83 m$^3$/min). This automatically charged the pressure chamber of the microfluidizer with compressed air.
2. The microfluidizer pressure was adjusted to 5000 PSI (344750 hPa).
3. The prepared Premix-II was added to the machine reservoir and the microfluidizer controls were turned to the full-on setting.
4. The Premix-II passed through the active cavitation chamber and exited into a collection vessel.
5. When all of the Premix-II was processed and collected, one cycle was completed.
6. Steps (1)-(5) were repeated four times, and/or until the processed liquid composition emerged into the collection vessel with a clear appearance.
7. The liquid composition was then aseptically filtered through a 0.2 micron membrane filter and stored at 4-8° C. until use.
8. The product of step 7, above, was then slowly mixed with the prepared Premix-I, so as to avoid foaming and disassociation of chemical constituents.
9. Fill up the final solution to the desired batch volume with WFI grade water, based on Tables 1-4. The final batch volume was 1 liter.

The pH was adjusted to 7.2±0.2.

The final inventive composition was then aseptically filtered through a 0.2 micron membrane into a sterile container for storage.

It appeared as an opaque milky white solution free of any particulate matter. The vesicle size has a great influence on the optical appearance of the nanoparticle dispersion. The smaller the particle the more transparent the solution will appear.

Example 2

Comparison of Liforlab and RNAlater as a Solution for Storing Tumor Explants or Biopsies The efficacy of Liforlab, prepared in example 1, for the preservation of the vitality of cells at room temperature are confirmed and evaluated relative to the preservative properties of RNAlater (Qiagen).

Samples

Immediately after preparation, biopsies of different tumors, or tumors explanted from animals are stored in at least 1 ml Liforlab or RNAlater (Qiagen, Neuss). The tissue biopsies can be cut, if necessary. Tissues pieces preferably have a maximum size of 0.5 cm$^3$, so the agent can rapidly diffuse the tissue. Preferably, the tissue has a size of 0.125 cm$^3$.

Methods

The tumor tissue is stored for a defined time, e.g. 3 days, in the solution Liforlab or RNAlater.

Together with the solution, the tumor tissue is then homogenized mechanically in a glass homogenisator or tapered tissue grinder (e.g., from Wheaton Science Products, NJ, USA). The homogenized tissue is transferred into a 15 ml tube with complete medium (e.g. L15 Medium with 10% FCS, inactivated, 1% non essential amino acids (100×, e.g. Biochrom AG, Berlin), 0.05% glucose, 0.0011% sodium hydrogen carbonate, Ciprobay 200) (3×4 ml) and washed (centrifugation at 150×g, 10 min, RT).

The suspension of cells is then transferred into a cell culture flask (50 ml, 17.5 cm$^2$) with enough medium to cover the floor. The cells are cultivated for at least 3 days at 37° C. in 5% $CO_2$ in the incubator without changing medium.

Medium is changed after visual control when the color of the medium changes from red to yellow. When the cells are sufficiently dense, the adherent cells are trypsinized and passaged.

For trypsinization, the medium is decanted and the cells that are still adherent are rinsed with PBS. 2 ml Trypsin-EDTA solution is added and incubated for 5 minutes at 37° C. in the incubator. The cells are separated from the bottom of the flasks by rapping the bottom softly, and they are transferred into 15 ml tubes with 10 ml of medium. After washing once with medium, the cells can be taken into culture again. After a third passage, the cells can be cryoconserved.

Results

The tissue stored in the Liforlab solution was soft and easy to homogenize. The cells made the resultant solution homogenously turbid. The tissue stored in RNAlater was solid and hard, and difficult to homogenize. Clumps of cell were easy to see in the solution.

After one week, the Liforlab-cells were growing well, whereas the RNAlater-cells were still swimming on top of the medium. The cells stored in Liforlab were regularly passaged for 6 weeks, and they proliferated. The cells were frozen in cryovials.

The attempt at culturing the RNAlater-cells was stopped after 12 days, as the cells were still swimming on top of the medium and it could not to be expected that the cells would still grow. The morphology of the cells was not homogenous (fragmented cells). The cells were not vital.

Summary

In contrast to cells from tumor explants stored in RNAlater, cells from tumor explants stored in Liforlab were vital and still capable of proliferation.

Example 3

Comparison of the Efficacy of Liforlab and RNAlater for Storing Tumor Cells and Stabilizing DNA With quantitative analysis of DNA from tumor tissue, the experiment establishes that Liforlab is equally capable of protecting DNA as RNAlater.

Samples

Immediately after preparation, biopsies of tumors generated from HCT8 cells explanted from nude mice were stored in at least 1 ml Liforlab or RNAlater (Qiagen). Tissues pieces preferably have a maximum size of 0.5 cm$^3$, so the agent can rapidly diffuse the tissue. Preferably, the tissue has a size of 0.125 cm$^3$.

1. Isolation of DNA with Conventional Methods

Methods

Lysis:

The tissue samples, 500 μL lysis buffer (10 mM Tris pH 8, 400 mM NaCl, 2 mM $Na_2$EDTA pH 8 to 8.2, autoclaved) and 20 μL RNase A (20 mg/mL) are transferred into a glass homogenisator and the tissue is homogenized as far as possible. The homogenate is transferred into a 50 mL falcon tube. The homogenisator is washed twice with 500 μL lysis buffer. This wash is added to the homogenate and softly vortexed. 100 μL 10% SDS are added, softly vortexed, then 25 μL of proteinase K (20 mg/mL) are added and softly vortexed.

The mixture is incubated at 55° C. for 2 hours or, better, at 37° C. over night in the water bath. After the digestion, 500 μL 5M NaCl are added (for salt precipitation of proteins, ca. 1.2 mol/L). The mixture is vortexed at middle level for ca. 5 seconds.

After a centrifugation in the cold centrifuge (4° C.) at 3410 g for 14 minutes, the supernatant that comprises the DNA is taken off and transferred into a new 15 mL polypropylene centrifuge tube. If any of the dell debris from the pellet is inadvertently taken up into the pipette, the sample is centrifuged again and the rest of the supernatant taken off.

Precipitation:

The supernatant is mixed with 2-2.5 volumes of 100 ethanol. The sample is stored for 30 to 60 minutes at −20° C. and afterwards centrifuged at 4° C. for 10 to 15 minutes at 3410 g. If the DNA visibly precipitates, the storage at −20° C. is not necessary. The supernatant is decanted carefully, taking care that the pellet is located at the upper wall so it cannot be lost in the decantation step. The DNA is washed with 1 mL 70% ethanol. It is then transferred into an autoclaved 1.5 mL tube with new 70% ethanol. The samples are centrifuged at 4° C. for 5 to 10 minutes at 3410 g, the supernatant is taken off, again looking after the pellet. The samples are again washed in 70° ethanol, centrifuged and the supernatant is taken off. The upper area inside the tube can be carefully dried with the tissue. The pellet should be dried in the air in the overturned tube. The DNA is taken up in 500 μL aqua injectabila. For better dissolving, the pellet can be incubated at 56° C. for 10 minutes. The samples are then stored at 4° C.

2. Isolation of DNA with Qiagen

Methods

Up to 25 mg of the stored biopsies are cut off on a cleaned slide, the weight is noted, and the tissue is prepared following the DNeasy protocol for animal tissues with the DNeasy tissue kit (Qiagen).

Photometric Analysis of DNA Quantity

For the photometric analysis, a 1:10 dilution is prepared and the extinction at 260, 280 and 320 nm is measured. The ratio of the extinction at 260 nm versus the extinction at 280 nm defines the purity of the DNA and should be between 1.4 and 1.8. The yield is calculated according to the following formula:

Extinction(260 nm)×50 μg/ml×dilution=μg/ml RNA

Results

Quantification of DNA prepared with conventional methods: For a tumor explanted from subcutaneous localisation at the shoulder, after 6 days storage at room temperature and then at 4° C., the yield per mg tissue was 5.56 μg with Liforlab and 6.36 μg with RNlater. For a tumor explanted from a subcutaneous localisation in the armpit and stored at 4° C., the yield was 6.44 µg with Liforlab and 4.94 µg with RNAlater. Results were confirmed by DNA gel electrophoresis.

Example 4

Comparison of the Efficacy of Liforlab and RNAlater for Storing Human Biopsies and Stabilizing RNA With quantitative analysis of RNA from tumor tissue, the experiment establishes that Liforlab is equally capable of protecting RNA as RNAlater.

Samples

Immediately after preparation, biopsies of different human tumors are stored in at least 1 ml Liforlab or RNAlater (Qiagen). Tissues pieces preferably have a maximum size of 0.5 $cm^3$, so the agent can rapidly diffuse the tissue. Preferably, the tissue has a size of 0.125 $cm^3$.

To prevent contaminations, it may be desirable to add Penicillin/Streptomycin to the Liforlab solution.

Methods
1. Preparation
    As preparation, the cutting area of an Ultra-Turrax hoinogenisator is cleaned in the ultrasound bath in 70% ethanol 30' prior to use. Slides and tweezers are purified with 70% ethanol. Gloves are worn throughout the procedure.
2. The tumor samples are stored for a defined time, e.g. 6 days at room temperature and then at 4° C. Up to 25 mg of the stored biopsies are cut off on a clean slide, transferred to a 5 ml cryovial and the weight is noted. 600 µL RLT buffer from the kit, but without β-mercaptoethanol, are added. The samples are homogenized in the ultra-turrax on ice 3× for 15 seconds and treated 4× for 5 seconds with ultrasound, level 3. After every sample, the equipment is cleaned with 70% ethanol. The homogenate is pipetted into an RNase free 1.5 ml tube and treated according to the "RNeasy mini protocol for the isolation of total RNA from animal tissue samples", Qiagen, April 2002. At point 5 the RNA is isolated and taken up in 1 to 2×30 µl of RNase free water.
3. Quantitative analysis of RNA
    Two methods are used for the quantitative analysis of the RNA in solution: Photometric analysis and real time PCR.
3.1 Photometric analysis
    For the photometric analysis a one in 100 solution (5 µl sample+495 µl water) is made and the extinction at 260, 280 and 320 nm is measured to analyze purity and yield. The extinction at 320 nm must be 0. The ration 260 nm:280 nm should be between 1.6 and 2.2. The yield is calculated according to the following formula:

Extinction(260 nm)×40 µg/ml×dilution=µg/ml RNA 3.2 Real time PCR
    The amount of RNA for the house-keeping enzyme GAPDH is analyzed by amplification of GAPDH, according to the method described in detail in A. H. Elmaagacli et al. (2001), Brit. Journal of Haematology, vol. 113, 1072-1075).
    In brief, the cDNA synthesis reaction and the PCR were performed in a single step with the LightCycler (Roche, Mannheim, Germany) using capillaries with a final volume of 10 µl. For RT-PCR-mixture, a commercially available buffer kit was used, including a reverse transkriptase, Taq polymerase, Tris-HCl, dNTP (Superscript, Gibco Life Tecnologies, Germany), 6 µM MgSO4, 0.14 µl RNase inhibitor (Roche, Germany), 10 pmol of the primer and 4 pmol of hybridization probe. The RT reaction was performed at 55° C. for 20 min. The amplification was continued with an internal denaturation at 95° C. for 20 sec followed by 55 cycles at 95° C. for 1 sec, 56° C. for 15 sec and 72° C. for 18 sec.

Examples of the results are set out in table 1 on the next page.

Example 5

A Comparison of Liforlab and Water for the Storing of Tumor Explants/Biopsies

Tumor biopsies from human necrotic or epithelial tissue of a carcinoma of the stomach were stored in water or Liforlab for 24, 48, 72 or 128 hours. Sections were cut and stained with HES.

The results show that Liforlab stabilizes the structure of the tissue much better than water.

Figure 1:
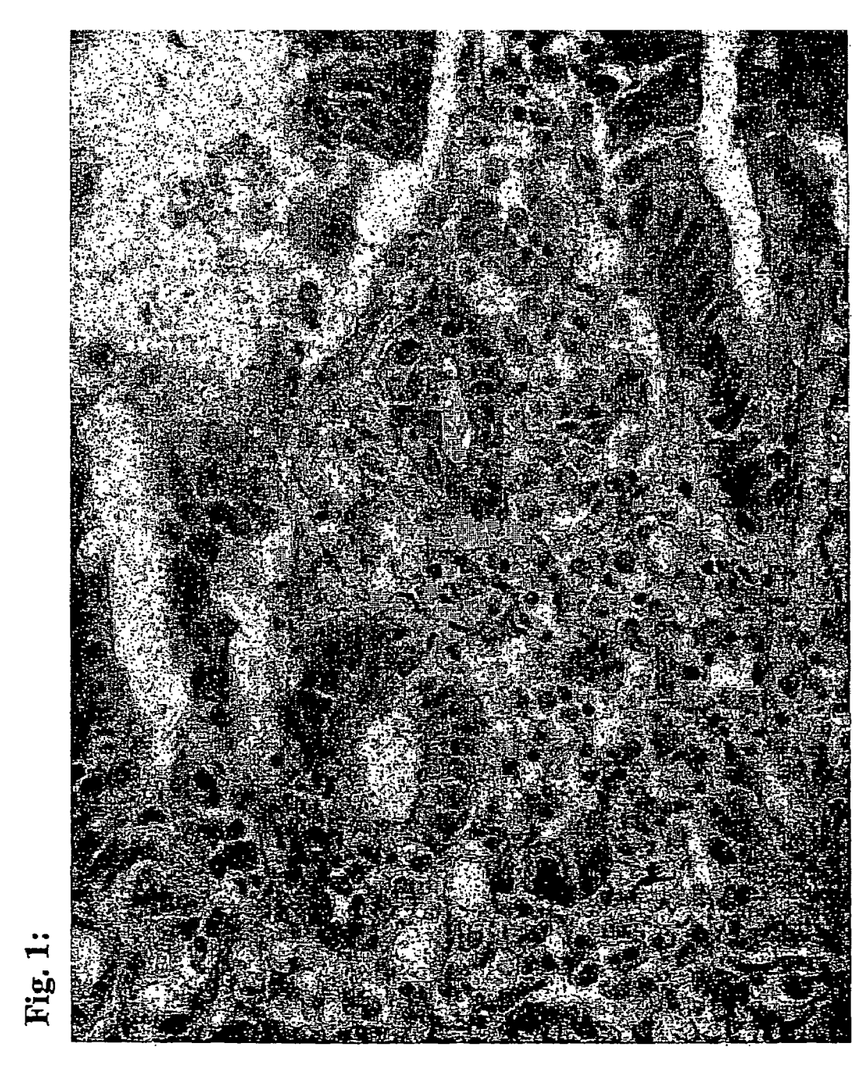
FIG. 1 shows a HES staining of a tumor biopsy from epithelial tissue of a carcinoma of the stomach at a magnification of 400×. The sample was stored in water for 24 hours prior to cutting.
Figure 2:
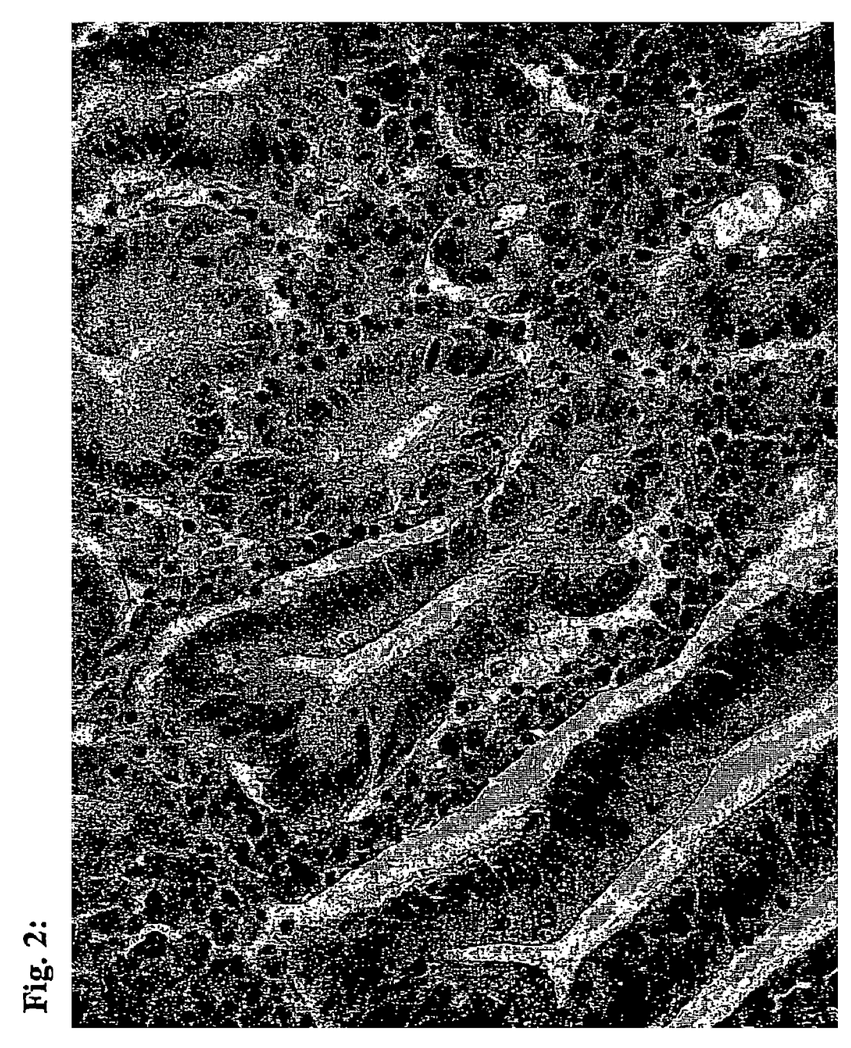
FIG. 2 shows a HES staining of a tumor biopsy from epithelial tissue of a carcinoma of the stomach at a magnification of 400×. The sample was stored in Liforlab for 24 hours prior to cutting.
Figure 3:
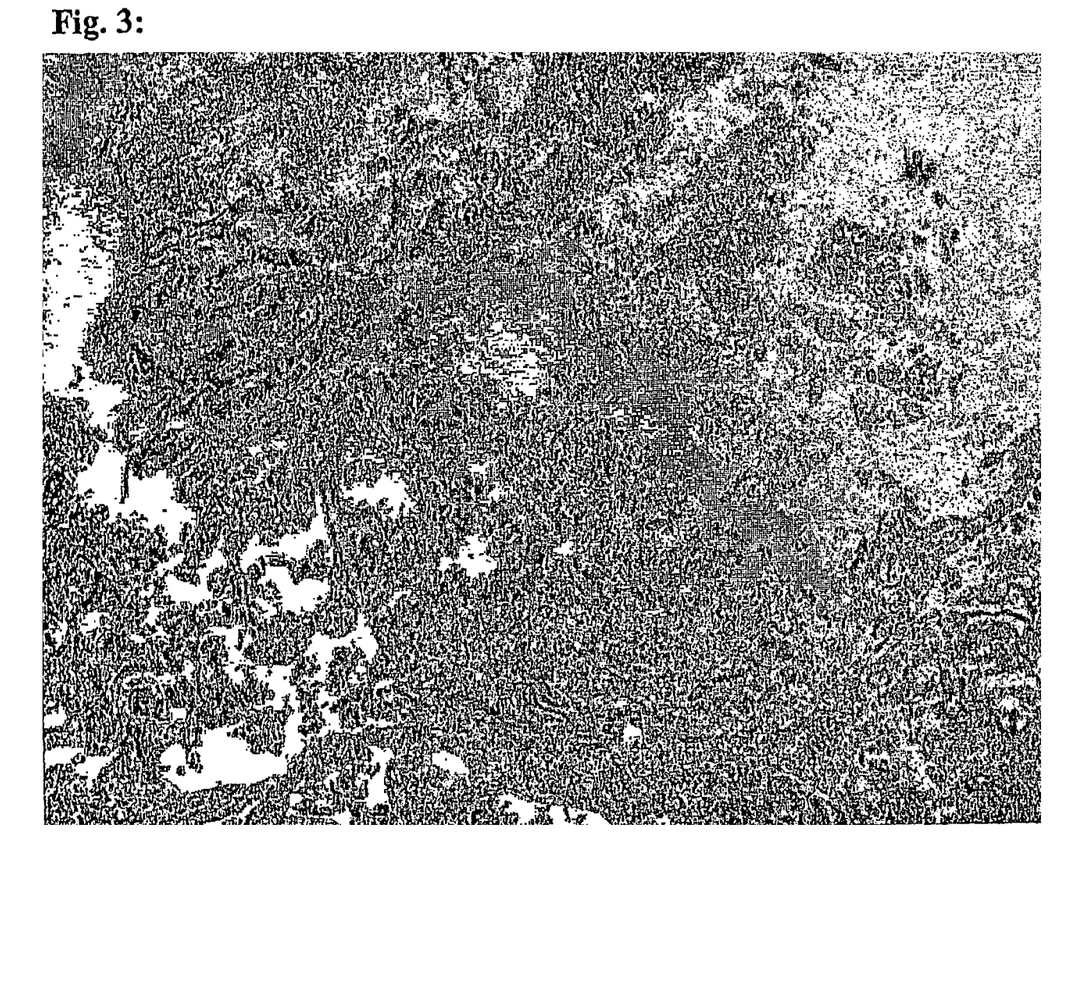
FIG. 3 shows a HES staining of a tumor biopsy from epithelial tissue of a carcinoma of the stomach at a magnification of 400×. The sample was stored in water for 72 hours prior to cutting.
Figure 4:
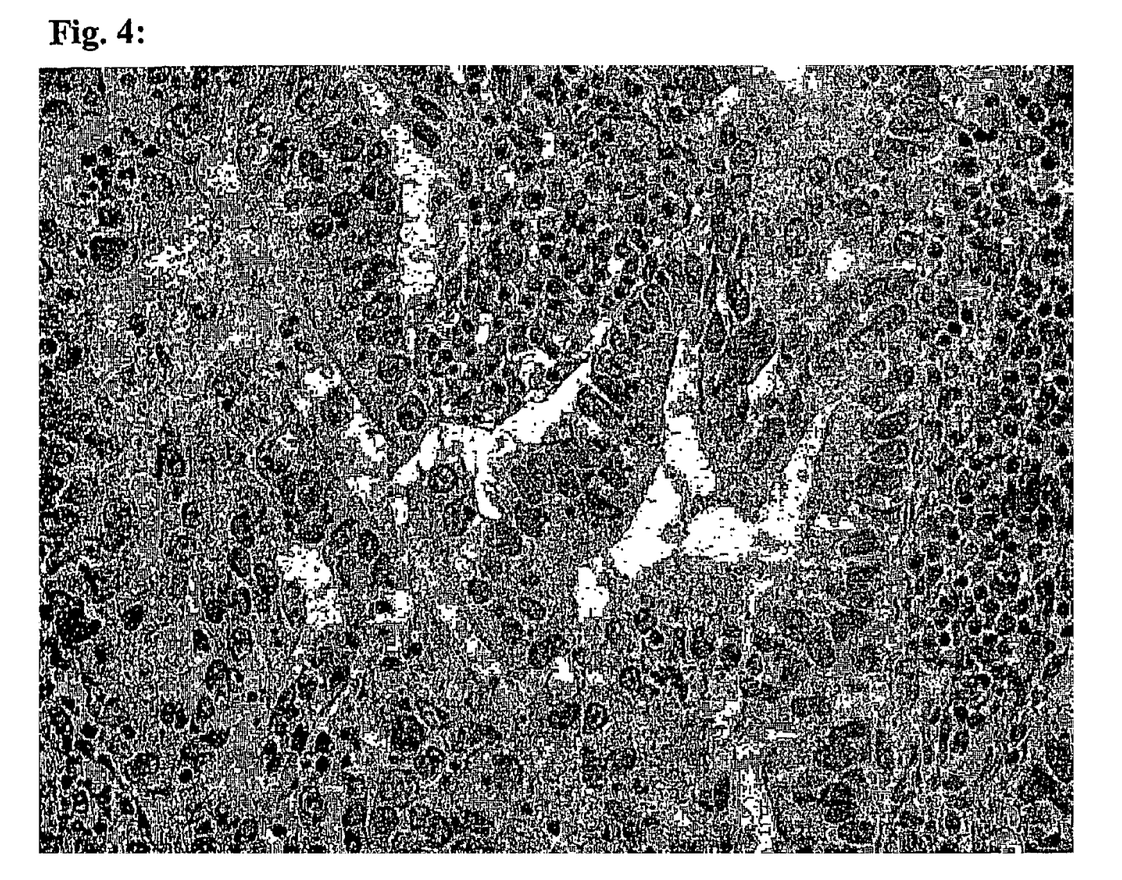
FIG. 4 shows a HES staining of a tumor biopsy from epithelial tissue of a carcinoma of the stomach at a magnification of 400×. The sample was stored in Liforlab for 72 hours prior to cutting.

Examples of the results are shown in FIG. 1 to 4. In FIG. 3, after storage of the epithelial tissue of the stomach in water for 72 hours, it is especially evident that the tissue is necrotic and degraded, wherein after storage in Liforlab, as shown in FIG. 4, the structure of the tissue is preserved.

TABLE 5

| Source of tumor tissue/biopsy | storage | time at RT | RNA/tissue (ng/mg) photometer | RNA/tissue (ng/mg) Realtime PCR |
|---|---|---|---|---|
| stomach corpus carcinoma | Liforlab | 3 d | 990 | 781.5 |
|  | RNAlater | 3 d | 320 | 559.0 |
| cardia carcinoma | Liforlab | 2 d | 420 | 127.5 |
|  | RNAlater | 2 d | 620 | 30.4 |
| osoephagus carcinoma | Liforlab | 2 d | 458 | 264.0 |
|  | RNAlater | 2 d | 634 | 370.8 |
| stomach lymphoma | Liforlab | 3 d | 260 | 452.7 |
|  | RNAlater | 3 d | 200 | 308.1 |
| osoephagus carcinoma | Liforlab | 1 d | 756 | 1142.5 |
|  | RNAlater | 1 d | 2436 | 940.2 |
| liver metastasis | Liforlab | 1 d | 86 | 185.0 |
|  | RNAlater | 1 d | 373 | 198.2 |

The invention claimed is:

1. A method for storing tumor cells in a composition, said method comprising:
    providing a composition and tumor cells, wherein said composition is enriched with oxygen and comprises a base nutritive medium and liposomes that comprise at least 0.00475 g/L cholesterol; and
    storing said tumor cells in said composition at temperatures in the range of −196° C. to 0° C.

2. The method of claim 1, wherein said tumor cells are stored in said composition for at least 1 day.

3. The method of claim 1, wherein said tumor cells are stored in said composition for at least 1 week.

4. The method of claim 1, wherein said tumor cells are stored in said composition for at least 1 month or at least several months.

5. The method of claim 1, wherein said tumor cells are stored in said composition for at least 1 year or at least several years.

6. The method of claim 1, wherein molecules in said tumor cells are not essentially degraded during storage and said molecules are selected from the group consisting of RNA, DNA, or RNA and DNA.

7. The method of claim 1, wherein said tumor cells can be analyzed via histological staining or in situ hybridization after storage.

8. The method of claim 1, wherein said tumor cells are capable of proliferation after storage.

9. The method of claim 1, wherein said tumor cells are stored in said composition first at a temperature in the range of 4 to 37° C.

10. The method of claim 1, wherein said tumor cells are first stored in said composition at room temperature and subsequently stored in said composition at a temperature in the range of −196 to 0° C.

11. The method of claim 1, wherein said tumor cells are stored in said composition at room temperature for at least 1 day and subsequently stored in said composition at a temperature in the range of −196 to 0° C. for at least 1 month and the RNA, the DNA, or the RNA and DNA in the tumor cells is essentially not degraded during storage at −196 to 0° C.

12. The method of claim 1, wherein said tumor cells are derived from a tumor tissue.

13. The method of claim 12, wherein said tumor tissue is a tumor biopsy.

14. The method of claim 1, wherein said tumor cells are derived from a human or a mammal.

15. The method of claim 12, wherein said tumor cells are derived from a solid tumor.

16. The method of claim 1, wherein said tumor cells are derived from a human biopsy stored at room temperature for 1 to 14 days in said composition and subsequently stored in said composition at a temperature in the range of −196 to 0° C. for at least 1 month, wherein the RNA, DNA, or RNA and DNA in said tumor cells is essentially not degraded during said storing at a temperature in the range of −196 to 0° C. for at least 1 month.

17. The method of claim 16, wherein said tumor cells are capable of proliferation after said storing at a temperature in the range of −196 to 0° C. for at least 1 month.

18. A method for freezing cells in a composition, said method comprising:
providing a composition and cells, wherein said composition is enriched with oxygen and comprises a base nutritive medium and liposomes that comprise at least 0.00475 g/L cholesterol; and
freezing said cells in said composition.

19. The method of claim 18, wherein said base nutritive medium comprises amino acids, salts, vitamins, nucleotides, carbohydrates, and anti-oxidants.

20. The method of claim 18, wherein said base nutritive medium comprises antimicrobial agents.

21. The method of claim 18, wherein said at least 0.00475 g/L cholesterol is 0.00475 g/L-0.00525 g/L cholesterol.

22. The method of claim 18, wherein said at least 0.00475 g/L cholesterol is at least 0.00525 g/L cholesterol.

23. The method of claim 18, wherein said liposomes comprise a growth factor, wherein said growth factor is selected from the group consisting of an epithelial growth factor, a hepatocyte growth factor, a platelet derived epithelial growth factor, a vascular endothelial growth factor, and combinations thereof.

24. A composition comprising tumor cells, a base nutritive medium, and liposomes, wherein said liposomes comprise at least 0.00475 g/L cholesterol and said composition is enriched with oxygen.

25. The composition according to claim 24, wherein said tumor cells are derived from tumor biopsies.

26. The composition according to claim 25, wherein said base nutritive medium comprises an agent selected from the group consisting of amino acids, salts, vitamins, nucleotides, carbohydrates, or anti-oxidants and combinations thereof; said tumor cells are derived from tumor biopsies; and said liposomes further comprise a growth factor selected from the group consisting of an epithelial growth factor, a hepatocyte growth factor, a platelet derived epithelial growth factor, a vascular endothelial growth factor, and combinations thereof.

27. A library of tumor biopsies comprising multiple compositions wherein each composition comprises tumor cells, a base nutritive medium, and liposomes, said liposomes comprise at least 0.00475 g/L cholesterol, said composition is enriched with oxygen, and each composition is stored in a separate container.

28. A method of screening comprising:
preparing a library of tumor biopsy compositions according to claim 27, and,
subjecting said library to diagnostic screening methods, drug-efficacy validation and/or methods for identifying anti-tumor drug targets.

29. A method for identifying anti-tumor substances comprising:
preparing a library of tumor biopsy compositions according to claim 27,
taking tumor cells from the prepared library into culture,
implanting the cultured cells into nude mice, and
testing potential anti-tumor substances in said nude mice,
wherein a potential anti-tumor substance would be considered to be an anti-tumor substance if the growth of the tumor is slowed, the number of metastases is lower, or the tumor regresses partially or totally as compared with control mice not treated with the potential anti-tumor substance.

30. A method of preparing a composition for storing cells, said method comprising:
preparing a base nutritive medium comprising physiologically compatible concentrations of water-soluble or dispersible nutrients and physiological salts;
preparing nanoparticles, which are liposomes comprising at least 0.00475 g/L cholesterol, fatty acids, and cellular growth factors; and
emulsifying said base nutritive medium and said nanoparticles to form a two phase composition, wherein said composition has an osmolality of at least about 300 mOsM/kg, does not contain a cryoprotective agent and is enriched with oxygen by bubbling oxygen through the composition until saturation.

\* \* \* \* \*

UNITED STATES PATENT AND TRADEMARK OFFICE
CERTIFICATE OF CORRECTION

PATENT NO. : 7,604,933 B2  Page 1 of 1
APPLICATION NO. : 10/556083
DATED : October 20, 2009
INVENTOR(S) : Ferdinand Bach et al.

It is certified that error appears in the above-identified patent and that said Letters Patent is hereby corrected as shown below:

On the title page item (54), replace the title as follows:

Methods for Storing Tumor Cells

Signed and Sealed this

Sixteenth Day of February, 2010

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,604,933 B2 |
| APPLICATION NO. | : 10/556083 |
| DATED | : October 20, 2009 |
| INVENTOR(S) | : Ferdinand Bach et al. |

Page 1 of 1

It is certified that error appears in the above-identified patent and that said Letters Patent is hereby corrected as shown below:

On the title page item (54) and at Column 1, line 1, replace the title as follows:

Methods for Storing Tumor Cells

This certificate supersedes the Certificate of Correction issued February 16, 2010.

Signed and Sealed this

Twenty-third Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,604,933 B2 Page 1 of 1
APPLICATION NO. : 10/556083
DATED : October 20, 2009
INVENTOR(S) : Ferdinand Bach et al.

It is certified that error appears in the above-identified patent and that said Letters Patent is hereby corrected as shown below:

On the title page item (54) and at Column 1, line 1, replace the title as follows:

Method for Storing Tumor Cells

This certificate supersedes the Certificates of Correction issued February 16, 2010 and March 23, 2010.

Signed and Sealed this

Twenty-ninth Day of June, 2010

David J. Kappos
*Director of the United States Patent and Trademark Office*

UNITED STATES PATENT AND TRADEMARK OFFICE
CERTIFICATE OF CORRECTION

PATENT NO. : 7,604,933 B2  Page 1 of 1
APPLICATION NO. : 10/556083
DATED : October 20, 2009
INVENTOR(S) : Ferdinand Bach et al.

It is certified that error appears in the above-identified patent and that said Letters Patent is hereby corrected as shown below:

Title Page,

(*) Notice: Subject to any disclaimer, the term of this patent is extended or adjusted under 35 U.S.C. 154(b) by 0 days.

should read (*) Notice: Subject to any disclaimer, the term of this patent is extended or adjusted under 35 U.S.C. 154(b) by 234 days.

Signed and Sealed this

Fourteenth Day of September, 2010

David J. Kappos
*Director of the United States Patent and Trademark Office*